US 6,965,434 B2

(12) United States Patent
Lounis et al.

(10) Patent No.: US 6,965,434 B2
(45) Date of Patent: *Nov. 15, 2005

(54) METHOD AND DEVICE FOR PHOTOTHERMAL IMAGING TINY METAL PARTICLES IMMERSED IN A GIVEN MEDIUM

(75) Inventors: Brahim Lounis, Bordeaux (FR); David Stephane Christophe Boyer, Mont de Marsan (FR); Philippe Tamarat, Gradignan (FR); Abdelhamid Maali, Pessac (FR); Michel Alain Gaston Julien Orrit, Oegstgeest (NL)

(73) Assignees: Centre National de la Recherche Scientifiques (C.N.R.S.), Paris (FR); Universite de Bordeaux 1, Talence (FR)

( * ) Notice: Subject to any disclaimer, the term of this patent is extended or adjusted under 35 U.S.C. 154(b) by 227 days.

This patent is subject to a terminal disclaimer.

(21) Appl. No.: 10/386,937

(22) Filed: Mar. 13, 2003

(65) Prior Publication Data

US 2004/0052292 A1 Mar. 18, 2004

Related U.S. Application Data

(60) Provisional application No. 60/410,305, filed on Sep. 13, 2002.

(51) Int. Cl.$^7$ .............................. G01B 9/02; G01J 5/02; G01J 5/00
(52) U.S. Cl. .................... 356/450; 250/341.6; 374/130
(58) Field of Search ............................... 356/502, 450; 374/43, 130; 250/341.1, 341.7, 341.6, 352, 351.8

(56) References Cited

U.S. PATENT DOCUMENTS 6,530,944 B2 * 3/2003 West et al. .................... 607/88
6,756,591 B1 * 6/2004 Lounis et al. ............ 250/316.1

(Continued)

OTHER PUBLICATIONS

Boyer et a l; "Photothermal Imaging of Nanometer–Sized Metal Particles Among Scatterers"; Science (Washington, DC), vol. 297, No. 5584, 2002, pp. 1160–1163; XP002242687.

(Continued)

*Primary Examiner*—Gregory J. Toatley, Jr.
*Assistant Examiner*—Patrick Connolly
(74) *Attorney, Agent, or Firm*—Stites & Harbison PLLC; Ross F. Hunt, Jr.

(57) ABSTRACT

A method and device for photothermal imaging tiny metal particles which are immersed in a given medium like a living cell. The given medium and immersed tiny metal particles are illuminated through separate phase reference laser beam and sensitive probe laser beam, with the sensitive probe laser beam undergoing through impingement on the given medium slight phase changes induced by photothermal effect due to a local heating thanks to a heating laser beam, in the absence of any substantial phase changes to the phase reference laser beam. Illuminating is performed by focusing the separate phase reference laser beam. The induced slight phase changes on the sensitive probe laser beam with reference to the phase reference laser beam are detected through differential phase interference contrast phenomenon so as to allow each of the tiny metal particles in the given medium to be imaged as an optical label.

16 Claims, 3 Drawing Sheets

U.S. PATENT DOCUMENTS

2004/0023415 A1 * 2/2004 Sokolov et al. ............. 436/518

OTHER PUBLICATIONS

Beil et al; "Chromatin texture analysis in three-dimensional images from confocal scanning laser microscopy"; Analytical and Quantitative Cytology and Histology, vol. 17, No. 5, 1995, pp. 323–331, Abstract; XP002242688.

Bialkowski; "Using An Optical Novelty Filter To Enhance Contrast In Photothermal Refraction Spectrometry"; $10^{th}$ International Conference on Photoacoustic and Photothermal Phenomena; Aug. 23–27, 1998; XP002242705.

Sheard et al.; "A new technique for imaging hard tissue by photothermal radiometric microscopy"; Scanning, vol. 11, No. 3, pp. 135–138; XP-002242689; Abstract.

Sönnichsen et al.; "Spectroscopy of single metallic nanoparticles using total internal reflection microscopy"; Applied Physics Letters, American Institute of Physics, vol. 77, No. 19; pp. 2949–2951, Nov. 6, 2000; XP-000970253.

Unknown; "Microscopic and spectroscopic imaging of the chemical state"; Practical Spectroscopy Series, vol. 16, p. Viii+495p; XP-002242690 Abstract.

* cited by examiner

METHOD AND DEVICE FOR PHOTOTHERMAL IMAGING TINY METAL PARTICLES IMMERSED IN A GIVEN MEDIUM

This application claims benefit of U.S. Provisional Application 60/410,305, filed Sep. 13, 2002.

The present invention relates generally to photothermal imaging tiny particles immersed in a given medium. More particularly the present invention relates to photothermal detection of metallic particles that can serve as a label for organelles or organic compounds and biomolecules included in a living cell.

Ambient optical detection of labeled molecules is presently limited to fluorescent dyes by photobleaching and semiconducting particles of nanometer size by blinking effects.

Nanometer-sized metal particles do not optically bleach and appear therefore particularly useful to serve as optical labels provided suitable detection process can be found.

An ideal optical label for large molecules should generate an intense optical signal, be of very small size, prove durable in time, as well as chemically inert and easy to bind to the molecule of interest in a controlled manner.

All present-day known optical markers fall short of the ideal label status definition.

The most common known labels, like fluorescent dyes, can usually be grafted to the molecule of interest. Their red-shifted fluorescence can be sifted very efficiently out of the given background.

The main drawback they are known to suffer however is photobleaching, i.e. an irreversible photochemical process leading from the excited fluorophore status to a non-fluorescent product.

Nanocrystals of II–VI semi-conductors, such as CdSe/ZnS have recently been proposed as optical markers. See particularly M. Bruchez, Jr., M. Moronne, P. Gin, S. Weiss, A. P. Alivisatos, in Science 281, 2013–6 1998 and W. C. Chan, S. Nie, in Science 281, 2016–8, 1998.

Although the semi-conductors resist bleaching longer than dyes, their luminescence brightness is liable to blinking while they are difficult to functionalize in a controlled way.

In contradistinction, metal particles are known to be currently used for single-particle or single-molecule tracking and immocytochemistry, see as an example W. Baschong, J. M. Lucocq and J. Roth, Histochemistry 83, 409–11 (1985) or J. W. Slot and H. J. Geuze, Eur J. Cell Biol 38, 87–93 (1985).

The above mentioned metal particles can either take the form of colloids with diameters ranging between a micron and a few nanometers or synthesized clusters with well-defined chemical structures. See for example P. A Frey and T. G. Frey. J Struct Biol 127, 94–100 (1999) or J. F. Hainfeld and R. D. Powell J Histochemistry Cytochemistry 48, 471–80 (2000).

Sub-micrometer metal particles down to diameters of 40 nm can be imaged using an optical microscope by means of their Rayleigh given, by illuminating in dark field at the plasmon frequency, with differential interference contrast (DIC) and video enhancement, or with total reflexion. See particularly S. Schultz, D. R. Smith, J. J. Mock and D. A. Schultz in Proc. Nati. Acad. Sci. USA 97, 996–1001 (2000), J. Gelles, B. J. Schnapp, M. P. Sheetz, in Nature 331, 450–3 (1988) and C. Sönnischen et al in Applied Physics Letters 77, 2949–2951 (2000) respectively for the three preceding mentioned alternatives.

While metal particles are very appealing optical labels owing to their absence of photobleaching phenomenon and optical saturation at reasonable exciting intensities, the Rayleigh given phenomenon they undergo decreases like the sixth power of their diameter, with the given signal being to be discriminated from a strong background.

Therefore the minimum size in diameter of a particle being detected in a living cell or in a given tissue is in practice well above the theoretical limit of 40 nm in diameter.

The well known Electron microscopy with its superior spatial resolution can well distinguish particles with diameters as low as 5 nm from organelles in a cell. See particularly J. M. Robinson, T. Takizawa, D. D. Vandre in J. Microscience 199, 163–79 (2000). Unfortunately Electron microscopy cannot be operative at ambient conditions.

The present invention provides for a method and device for photothermal imaging tiny metal particles immersed in a given medium particularly adapted to remedy the drawbacks suffered by the methods, processes and devices of the prior art.

More particularly one object of the present invention is to provide for a method and device for photothermal imaging small particles, metal particles, down to 1 nm in diameter at ambient conditions with an optical microscope.

Another object of the present invention is thus to provide for a method and device for photothermal imaging small particles allowing thus to correlate single particle, as labels, with optical microscopic images, without any need for conjugation to bulky fluorescent antibodies.

Another object of the present invention is thus to provide for a very high sensitive method and device particularly adapted to allow an efficient, reproductible and promising way to visualize low amounts of proteins, biomolecules or organelles in living cells.

The method for photothermal imaging tiny metal particles immersed in a given medium which is the object of the invention consists at least in illuminating this given medium and immersed tiny particles through separate phase reference laser beam and sensitive laser beam, the sensitive probe laser beam undergoing through impingement on the given medium slight phase changes induced by photothermal effect due to a local heating within the given medium in the absence of any susbstantial phase changes to the phase reference laser beam.

The slight phase changes on the sensitive probe laser beam with reference to the phase reference laser beam are thus detected through differential phase interference contrast phenomenon, with each of the tiny metal particles immersed in the given medium being imaged as an optical label.

The device for photothermal imaging of tiny metal particles immersed in a given medium which is the object of the invention comprises a unit for illuminating part of this given medium and immersed tiny particles through separate phase reference laser beam and sensitive probe laser beam, the sensitive probe laser beam undergoing through impingement of the sensitive probe laser beam on the given medium slight phase changes induced by photothermal effect due to a local heating within the given medium in the absence of any substantial phase changes to the phase reference laser beam.

It further comprises a unit for detecting these slight phase changes on the sensitive probe laser beam with reference to the phase reference laser beam through a differential phase interference contrast phenomenon. A unit is provided for imaging each of the tiny metal particles immersed within the given medium as an optical label from the differential phase interference contrast phenomenon.

The objectives, advantages and particulars of the present invention will be understood by reading the following detailed description and accompanying drawings, in which:

FIG. 1B shows particular embodiments of given steps of the method of the invention as shown at FIG. 1a;

The following detailed description contains many particulars for the purposes of sole illustration. These specifics are given as exemplary details belonging to the scope of the invention.

Figure 1A:
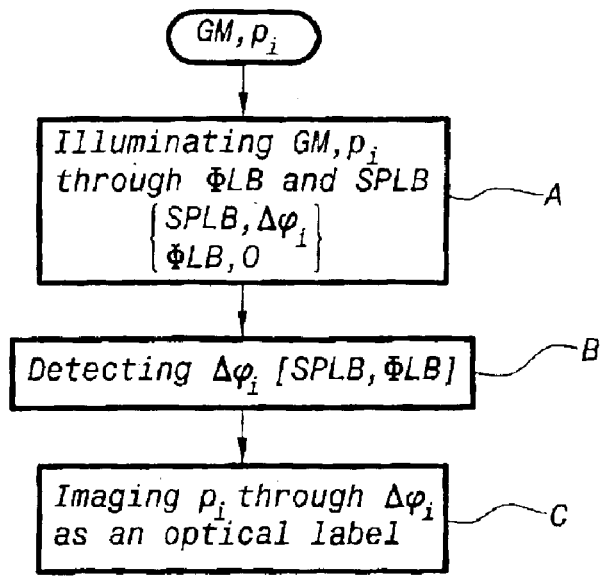
FIG. 1A shows a general flowchart of the method for photothermal imaging tiny metal particles immersed in a given medium according to the present invention.
Figure 1B:
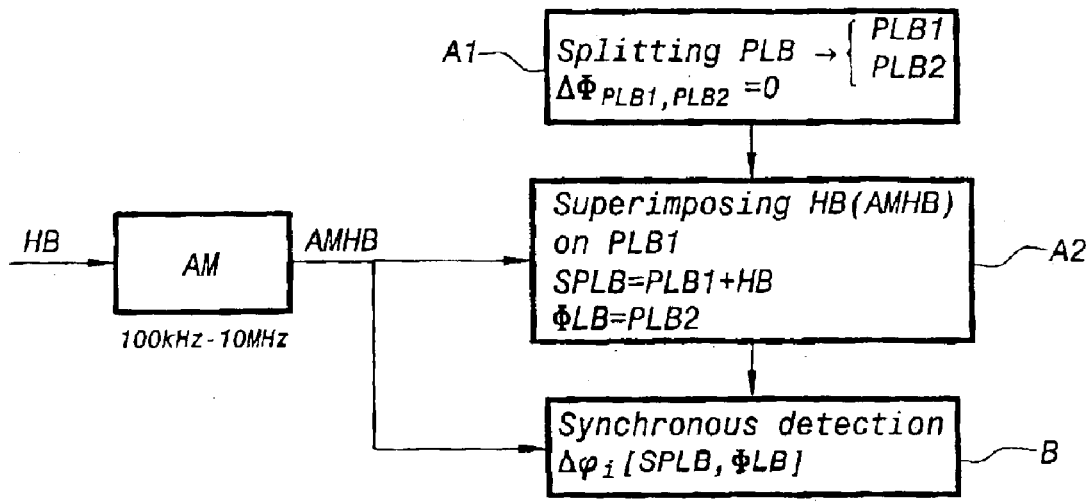

The method for photothermal imaging tiny metal particles immersed in a given medium which is object of the invention is now disclosed in relation with FIGS. 1A and 1B. As an example, the given medium in which the tiny particles are immersed into should be understood as a scattering medium or a non scattering medium including scatterers or the like.

As shown at FIG. 1A the method of the invention consists, in a step denoted A, in illuminating the given medium, which is denoted GM, and immersed tiny particles, denoted $p_i$, through separate phase reference laser beam denoted $\phi$LB and sensitive probe laser beam denoted SPLB.

As a consequence, the sensitive probe laser beam SPLB undergoes through impingement on the given medium GM slight phase changes induced by photothermal effect due to a local heating within this given medium GM, in the absence of any substantial phase changes to the phase reference laser beam $\phi$LB.

The phase relationship of each of the phase reference laser beam and sensitive probe laser beam is denoted SPLB, $\Delta_{\phi i}$ $\phi$LB, 0

With reference to FIG. 1A, step A is followed by a step denoted B consisting in detecting the slight phase changes on the sensitive probe laser beam SPLB, with respect to the phase reference laser beam $\phi$LB.

The detection of the slight phase changes can be conducted, according to one of the advantageous aspects of the method of the invention, through a differential phase interference contrast phenomenon.

The detection operation is illustrated by the following relationship $\Delta_{\phi i}$ (SPLB, $\phi$LB)

From the preceding relationship it is understood that each slight phase changes induced by photothermal effect in the vincinity of each tiny metal particle $p_i$, with these slight phase changes being denoted $\Delta_{\phi i}$, is obtained thanks to the phase interference contrast phenomenon of both phase reference laser beam $\phi$LB and sensitive probe laser beam SPLB and thus detected.

Accordingly each of the tiny metal particles $p_i$ which are immersed in the given medium GM can thus be imaged as an optical label at step C shown at FIG. 1A.

The mode of operation of the method of the invention as disclosed in relation with FIG. 1A will be now justified on physical grounds below.

Because of the optical absorption of a small metal particle decreases as only the third power of its diameter, the absorption phenomenon will prevail over the given phenomenon below a given particle size.

The absorption cross section of a gold particle of 5 nm in diameter is about 3 $nm^2$ at 514 nm wavelength. This absorption value is more than two orders of magnitude greater than that of an organic fluorophore at room temperature.

Such a strong absorption value gives rise to a photothermal effect, i.e. a temperature rise around the particle when it is illuminated by a laser beam.

According to the method of the invention this temperature change is optically detected by a sensitive interference method akin to DIC (for differential interference contrast) with these particles being thus fully adapted to operate as optical labels.

A particular embodiment of the method of the invention, particularly its above mentioned steps A and B will be now disclosed with reference to FIG. 1B.

As shown at FIG. 1B step A of illuminating the given medium GM and immersed tiny particles $p_i$ may consist at a sub-step A1 in splitting a probe laser beam, denoted PLB, into a first and a second probe laser, beam each denoted $PLB_1$ and $PLB_2$ respectively, with the first and second probe laser beam undergoing the same phase relationship on separate optical path.

The phase relationship between first and second probe laser beam is denoted $\Delta\phi_{PLB1,PLB2}=0$ Sub-step A1 is thus followed by a subsequent sub-step A2 consisting in superimposing on one of the first and second probe laser beam a heating laser beam, denoted HB, propagating on the same optical path as that of the first or second probe laser beam it is superimposed to. As an example, at sub-step A2 at FIG. 1B, the heating laser beam is superimposed on the first probe laser beam denoted $PLB_1$.

Consequently, the first probe laser beam $PLB_1$ and superimposed heating laser beam HB actually form the above mentioned sensitive probe laser beam SPLB, as already disclosed in relation with FIG. 1A. The second probe laser beam $PLB_2$ thus forms the phase reference laser beam $\phi$LB as already disclosed in relation with FIG. 1A.

The operation of superimposing a heating laser beam HB to one of the probe laser beam, $PLB_1$, and assigning the second probe laser beam $PLB_2$ as phase reference laser beam $\phi$LB is denoted through the relationship $SPLB=PLB_1+HB$ $\phi LB=PLB_2$.

With reference to FIG. 1B the step of detecting the slight phase changes step, denoted B at FIG. 1A, can be thus implemented preferably trough synchronous detection, as shown at step denoted B at FIG. 1B. To this end, the method of the invention may preferably consist in amplitude modulating the heating laser beam HB at a given frequency and thus synchronously detecting the slight phase changes through differential phase interference contrast phenomenon. The frequency for amplitude modulating the heating laser beam HB can be chosen in the range 100 kHz–10 MHz.

The above mentioned frequency can be chosen so that a given volume of the given medium overlaps the focal spot of the sensitive probe laser beam SPLB focused on the given medium GM.

The mode of operation of the method of the invention as shown at FIG. 1B will be now justified below.

While photothermal detection is fully known from the prior art particularly using a thermal lens effect to detect very low concentrations of absorbing molecules in liquid solutions, the method of the invention, as illustrated at FIG. 1B, makes use of a very sensitive polarization interference method which allows the detection of slight phase changes. A full description of such a method has been published by P. Cleizes, A. C. Boccara, and H. Saint-James, in optic letters 22 (1529–1531 99 97).

Introducing further an amplitude modulation of the heating laser beam HB and then a synchronous detection of the small phase changes induced through photothermal effect on the sensitive probe laser beam SPLB allows hence to improve the noise rejection by means of the high frequency modulation.

The volume undergoing a significant temperature modulation is determined by the dumping of heat waves at the modulation frequency. Consequently, the frequency for amplitude modulation is thus chosen such that this volume overlapses the focal spot of the sensitive probe laser beam SPLB.

The photothermal contrast can thus be implemented on a standard optical microscope, such a mode of operation being used with organic or biological samples in a given medium, without introducing background.

A particular embodiment of the method of the invention in which the phase changes detection is performed on reflected phase reference and sensing probe laser beam, after reflection by the given medium and its glass cover slip interface, will be now explained with reference to FIG. 2.

Figure 2:
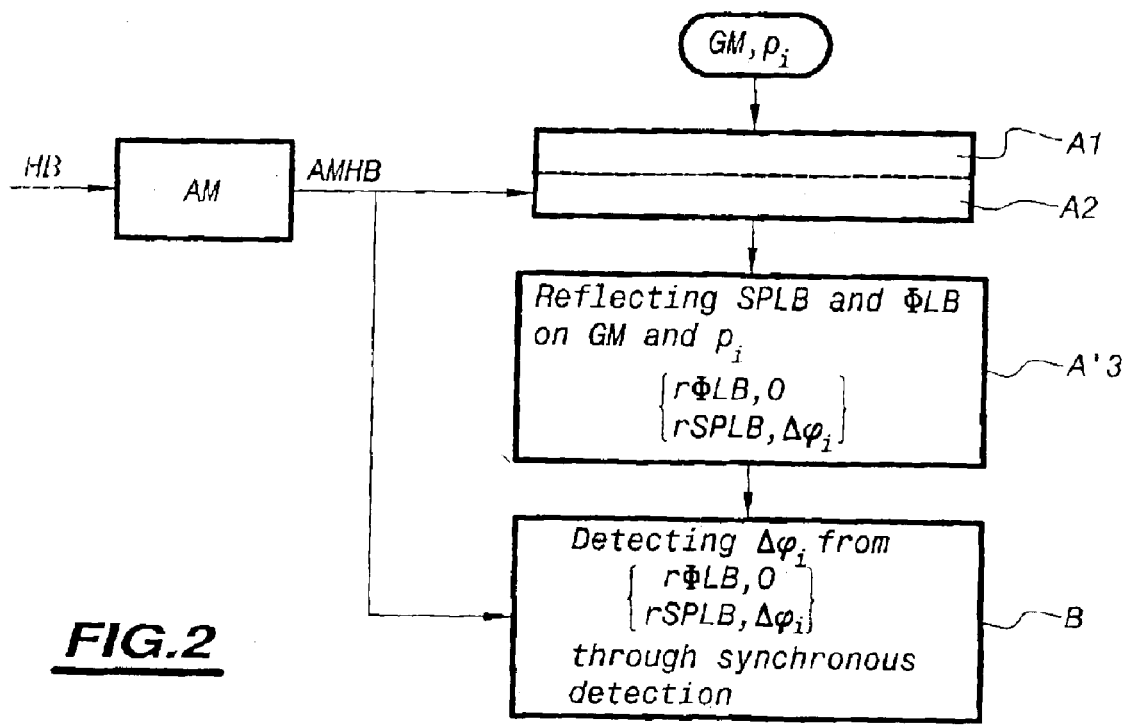
FIG. 2 shows another exemplary embodiment of the method according to the invention, in which the phase changes detection is performed on reflected phase reference and sensing probe laser beam, after reflection by the given medium and its cover slip interface.

As shown at FIG. 2, it should be understood that the method of the invention according to this embodiment actually comprises the sub-steps A1 and A2 as already disclosed with reference to FIG. 1B.

It further comprises at least a sub-step A'3 consisting in illuminating the given medium GM and immersed tiny particles through separate phase reference laser beam and sensitive probe laser beam, denoted SPLB and φLB respectively.

Thanks to this illumination a reflected phase reference laser beam and a reflected sensitive probe laser beam denoted rφLB and rSPLB respectively are generated, with the reflected sensitive probe laser beam undergoing through impingement of the sensitive probe laser beam on the given medium GM slight phase changes induced by photothermal effect, due to the local heating within this given medium, in the absence of any substantial phase changes to the reflected phase reference laser beam rφLB.

The phase relationship undergone by the reflected phase reference laser beam rφLB and the reflected sensitive probe laser beam rSPLB verify the relation rφLB, 0 rSPLB, $\Delta_{\phi i}$.

Sub-step A'$_3$ can be thus followed by step B with a detection of the slight phase changes taking place on the reflected sensitive probe laser beam with reference to the reflected phase reference laser beam through differential phase interference contrast phenomenon.

Figure 3:
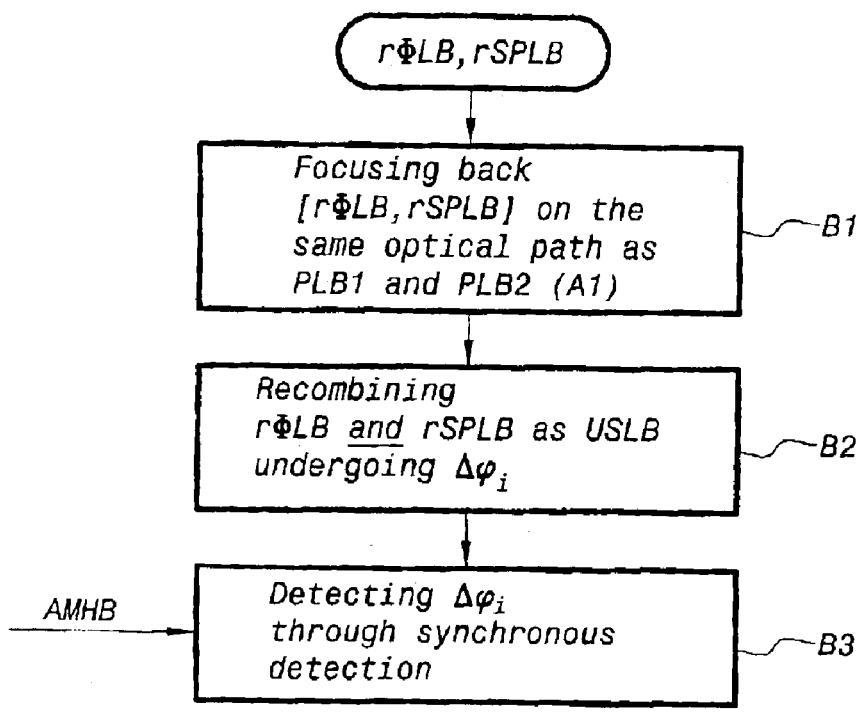
FIG. 3 shows a particular exemplary embodiment of the method of the invention in which a common processing of the transmitted phase reference and sensing probe laser beam and the reflected phase reference and sensing probe laser beam shown at FIG. 2 is disclosed.

A particular mode of operation of the method of the invention whichever it is performed thanks to the reflected sensitive probe laser beam and reflected phase reference laser beam on the given medium GM, will be now disclosed with reference to FIG. 3.

As shown at FIG. 3 the method of the invention may consist at a step B$_1$ in focusing back the reflected phase reference laser beam and reflected sensitive probe laser beam denoted rφLB, rSPLB on the same optical path as that of the first and second probe laser beam PLB$_1$ and PLB$_2$, as already disclosed in relation to sub-step A1 of FIG. 2.

Sub-step B1 is thus followed by a sub-step B2 consisting in recombining the focused reflected phase reference and reflected sensitive probe laser beam for retro-reflected transmitted phase laser beam and transmitted sensitive probe laser beam to a unique sensing laser beam denoted USLB in which the differential phase interference phenomenon $\Delta_{\phi i}$ is induced.

The recombination operation is denoted recombining rφLB and rSPLB to USLB undergoing $\Delta_{\phi i}$.

Figure 4:
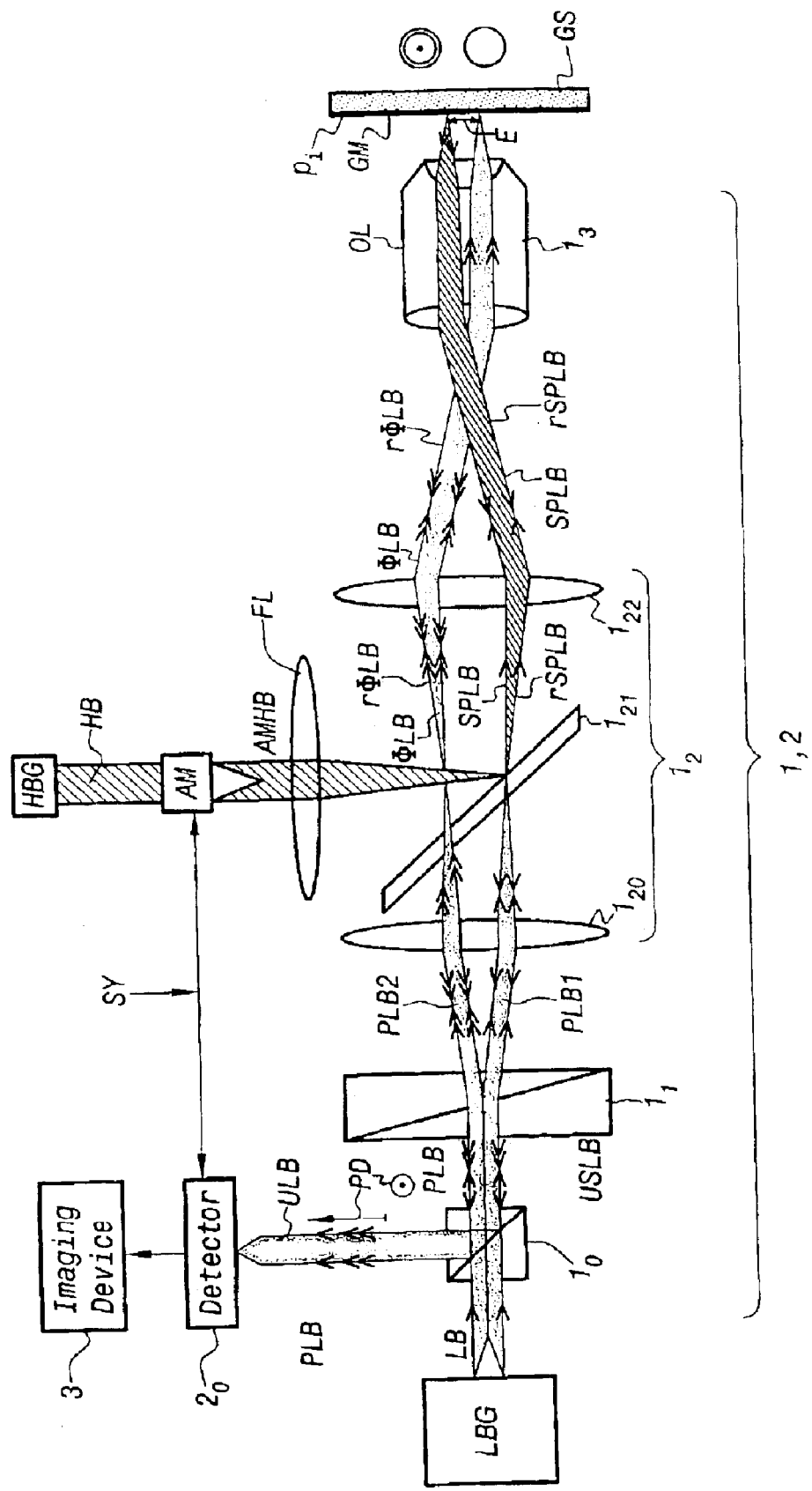
FIG. 4 shows a general view of a device for photothermal imaging tiny metal particles immersed in a given medium according to a particular embodiment of the invention, this device being more particularly adapted to operating the method of the invention as shown at FIGS. 1A, 1B, 2 and 3.

A fully detailed description of a preferred embodiment of a device for photothermal imaging, tiny metal particles immersed in a given medium according to the invention is now given with reference to FIG. 4.

With reference to FIG. 4, the device of the invention comprises a unit 1 for illuminating part of the given medium denoted GM and immersed tiny particles p$_i$, through separate phase reference laser beam and sensitive probe laser beam denoted φLB and SPLB respectively. The sensitive probe laser beam undergoes through impingement on this given medium GM slight phase changes induced by photothermal effect due to local heating within the given medium in the absence of any substantial phase changes to the phase reference laser beam φLB as already disclosed in the present description.

As shown at FIG. 4, the device of the invention also includes a unit for detecting the slight phase changes on the sensitive probe laser beam, this detecting unit being denoted 2 and adapted to perform a detection through a differential phase interference contrast phenomenon, with reference to the phase reference to the phase reference laser beam φLB.

According to a particular advantaging feature of the device of the invention, the unit 1 for illuminating and the unit 2 for detecting may substantially comprise the same optical components, as it will be disclosed in more details later on in the description.

A unit 3 for imaging each of the tiny metal particles p$_i$ immersed in the given medium GM as an optical label is provided with the imaging being performed from the differential phase interference contrast phenomenon.

As shown on FIG. 4, the unit 1 for illuminating may comprise a laser beam generator denoted LBG adapted to generate a laser beam LB. The laser generator LBG may consist of an He—Ne laser generator at a 633 nm wavelength. The generated laser beam LB is polarised horizontally with a polarisation direction PD of the probe laser beam PLB shown on FIG. 4 as orthogonal to this figure. Polarisation takes place through a polarizing cube denoted 1$_0$, with the probe laser beam PLB being understood as a polarised probe laser beam.

The unit 1 for illuminating further comprises a sub-unit for splitting the probe laser beam PLB to a first and second probe laser beam, denoted PLB$_1$ and PLB$_2$, with the first and second probe laser beam undergoing the same phase relationship on separate optical paths as shown on FIG. 4. Preferably, the sub-unit for splitting 1$_1$ may consist of a Wollaston prism.

The unit 1 for illuminating further comprises a heating laser beam generating unit denoted HBG adapted to generating a heating laser beam denoted HB. The heating laser beam generating unit may consist of a laser generating unit at 514 nm wavelength delivering the heating laser beam HB to a further sub-unit for amplitude modulating the heating laser beam HB. On FIG. 4, the amplitude modulating unit is denoted AM. The amplitude or intensity modulating unit AM may consist of an electro-optic or acousto-optic modulator synchronised through a synchronising signal SY. The amplitude or intensity modulation may take place at high frequency, preferably in the range 100 kHz–10 MHz.

The unit 1 for illuminating as shown on FIG. 4 is further provided with a sub-unit denoted $1_2$ for superimposing the heating laser beam, particularly the amplitude modulated heating laser beam AMHB on one of the first and second probe laser beam $PLB_1$ or $PLB_2$.

As shown on FIG. 4, as a non limitative example, superimposing of the heating laser beam AMHB takes place on the first probe laser beam $PLB_1$ with a superimposed heating laser beam propagating thus on the same optical path as that of first probe laser beam $PLB_1$.

The superimposed heating laser beam AMHB and the first probe laser beam $PLB_1$ propagates thus on the same optical path so as to constitute the sensitive probe laser beam denoted SPLB while the other one of the first and second probe laser beam, actually the second probe laser beam $PLB_2$, constitutes thus the phase reference laser beam φLB.

As shown on FIG. 4, sub-unit $1_2$ for superimposing may consist of a focusing length denoted FL, adapted to focusing the amplitude modulated heating laser beam AMHB, together with a telecentric system which can be formed thanks to a first lens denoted $1_{20}$, a semi reflecting glass slide denoted $1_{21}$ and a second lens denoted $1_{22}$. As shown on FIG. 4, the heating laser beam and the first probe laser beam $PLB_1$ are focused on the same area of the output phase of the semi reflecting glass slide $1_{21}$, such a feature allowing thus the superimposing operation of both laser beams to be performed.

According to a preferred embodiment of the device of the invention as shown at FIG. 4, subunits $1_1$ and $1_2$, i.e. the Wollaston prism and the telecentric system, can be advantageously replaced by a unique Nomarski prism.

As it will be understood from FIG. 4, the unit 1 for illuminating further comprises a sub-unit $1_3$ adapted to focusing the phase reference laser beam φLB and the sensitive probe laser beam SPLB at separate locations on the given medium GM.

The separate locations at which both preceding laser beams are focused, should be understood as focusing points separated by a distance denoted E with this distance allowing the phase reference laser beam φLB not to undergo the local heating generated by the sensitive probe laser beam SPLB and thus the slight phase changes induced on the latter.

According to the embodiment shown at FIG. 4, the device of the invention is more particularly adapted to detecting the slight phase changes through photo thermal effect which are induced on reflected phase reference laser beam denoted rφLB and reflected sensitive probe laser beam denoted rSPLB with these reflected laser beams being actually reflected by the given medium GM, tiny metal particles immersed therein and cover slip interface.

To that end, in the device of the invention as shown on FIG. 4, the given medium GM is deposited on a glass cover slip GS for example, so as to allow the most important part of the reflected phase preference laser beam and reflected sensitive probe laser beam to emanate from the sole given medium and tiny particles immersed therein.

More particularly, the objective length OL is fully adapted, thanks to a 3D moving table, to allow a full focusing of the reference laser beam φLB and sensitive probe laser beam SPLB on the given medium GM. The 3D moving table may consist of a piezo 3D table.

It should be understood that in this situation the phase reference laser beam and sensitive probe laser beam are actually focused in the object plane of the objective lens OL with the given medium being thus placed in coincidence with this object plane.

While the objective lens OL might well allow to focusing the reference laser beam and sensitive probe laser beam on the given medium GM and tiny particles $p_i$, operating the detection of the light phase changes undergone by the sensitive probe laser beam over the reference laser beam would afterwards imply recombining the sensitive probe laser beam SPLB and phase reference phase laser beam φLB so as to induce the differential phase interference phase phenomenon.

Operating this way would thus imply providing bulky and costly optical equipments adapted to recombine the above-mentioned laser beams at the level of the given medium GM.

To remedy the above-mentioned drawback, according to one of the features of interest of the invention, all the components and sub-units embodying the illuminating unit 1 are thus adapted to partially serve as the detecting unit 2 as previously mentioned in the description.

To that end, as shown on FIG. 4, the focusing unit $1_3$ is adapted to transmitting back the reflected phase reference laser beam and reflected sensitive probe laser beam denoted rφLB and rSPLB respectively with these reflected laser beams emanating from the given medium GM.

The reflected sensitive probe laser beam rSPLB and phase reference laser beam rφLB propagate thus back along corresponding optical paths of the sensitive probe laser beam and phase reference laser beam illuminating the given medium. It should be understood on the light of FIG. 4 that the whole system formed by the given medium GM and the objective lens OL are adapted to allow a corresponding reflecting of the phase laser beam and sensitive probe laser beam along the same optical paths as that of impinging phase laser beam and sensitive probe laser beam respectively.

In the same way, sub-unit $1_2$ for combining, sub-unit $1_1$ for splitting and sub-unit $1_0$ for polarising embodying the illuminating unit 1 are fully adapted to constitute a recombining sub-unit allowing the reflected phase reference and sensitive probe laser beam to a unique laser beam denoted USLB in which the differential phase interference phenomenon is induced.

As shown on FIG. 4, the unique laser beam USLB after recombination, reflection and transmission by the polarising cube or sub-unit $1_0$ is vertically polarised and thus sent to a detecting unit or detector $2_0$. The detecting unit $2_0$ may consist of a fast photo diode for instance. Detection can take place under control of the synchronising signal SY in order to allow a synchronous detection to be performed.

The detecting unit $2_0$ is thus connected to the imaging device 3 thus to allow a full imaging of the given medium GM and tiny metal particles immersed in this medium.

The mode of operation of the detecting unit $2_0$ can be summarised as follows:

While the probe laser beam PLB is generated, as an example, in the red domain of wavelength, the heating laser beam belongs to the range of the green wavelength.

The amplitude modulated heating laser beam AMHB induces a periodic phase difference between the transmitted sensitive probe laser beam and transmitted phase reference laser beam which gives rise to a modulation of the detected red intensity.

Consequently, a red path filter can be used to eliminate green stray light from the heating beam. A locking amplifier can thus detect the variations of the red intensity and thus the dephasing between the retro-reflected transmitted sensitive probe laser beam and transmitted phase reference laser beam as the modulation frequency of the heating laser beam. The lock-in detection can thus be performed at the modulation frequency so as to perform the synchronous detection with an integration time of 10 milliseconds for example. Microscopic images are thus obtained thanks to the imaging device 3 by scanning the sample of given medium with the focused laser beam and sensitive probe laser beam or plurality of sets of these laser beams.

The embodiment of the device of the invention as shown on FIG. 4 needs an illuminating power at each spot at which the phase reference laser beam and sensitive probe laser beam in red light are focused to about 2.5 mW while the maximum power reaching the fast photo diode is only about 150 microwatts.

Several physical relationships of the mode of operation of the device of the invention and corresponding method thereof will be given below. The elevation to temperature T caused at a distance r of a modulated point source of heat with power P $[1+\cos(\overline{\omega t})]$ in a homogenous medium is derived from the equation of heat conduction and is given by:

$$T - T_0 = \frac{P}{4\pi\kappa r}[1 + \exp(-r/R)\cos(\varpi t - r/R)] \quad (1)$$

where $T_0$ is the ambient temperature, $\kappa$ is the thermal conductivity of the medium and R is the characteristic length for heat diffusion at frequency $\omega$ given as $\sqrt{2\kappa/\omega C}$ (C is the heat capacity of a unit volume of the medium). The phase difference between the two red beams embodying the phase reference laser beam and sensitive probe laser beam is proportional to the temperature change averaged over the spot size. The signal should be roughly constant for frequencies $\omega < \omega_s = 2\kappa C^{-1} R_s^{-2}$ (such that R is larger that the spot size $R_s$), and should decrease for $\omega > \omega s$. Typical values for the heat diffusion constant of organic materials lead to $\omega_s$ values around 1 MHz.

Samples were prepared by spin-coating a drop of an aqueous solution of poly-vynil-alcohol (PVA, 1% weight) doped with gold nanoparticles, on a microscope cover slip. The gold particles had diameters of 20, 10 and 5 nm with half-maximum dispersions in diameters of 2, 1 and 0.6 nm, respectively, according to the manufacturer's specifications. The three-dimensional representation of a photothermal image of 5-nm diameter gold nanoparticules has shown no background from the substrate, which means that the signal arises from the only absorbing objects in the sample, namely the gold nanospheres. These small nanoparticles were detected with a remarkably large signal-to-noise ration (S/N>10). Smaller particles with 2.4 nm diameter with a S/N~2 can be thus imaged. A histogram of peak heights for about 200 imaged spots has shown a fairly narrow unimodal distribution (in good agreement with the manufacturer's specifications), which clearly confirmed that the spots stem from individual nanospheres. Stronger peaks that could have been attributed to pairs of particles or to higher order aggregates were extremely rare. Any weaker spots even at a much higher heating power could not be found.

Further trials have shown that the imaging mechanism is indeed photothermal by determining the dependance of the signal with the particle size and the heating laser power. The signal intensities for 5, 10, and 20 nm diameter spheres varied linearly with the volume of the particles. This signal is perfectly linear in the heating power with no sign of saturation in the range of intensities which were used in the experiments (up to 20 MW/cm2 for the smallest spheres). A rough calculation of the temperature increase of the 5-nm spheres for this power gave about 15 K at the surface of the sphere, a temperature increase for which no significant change in optical properties did occur.

Investigation on how the signal depends on the distance between the green and red spots have also been conducted. Equation 1 predicts a signal decreasing as the inverse square of the distance, at large enough distances. The decrease that has been observed was indeed steeper that 1/r, although the distance range was too narrow to determine the exponent. As expected, however, the signal was largest when the green spot of the heating laser beam overlapped one of the red spots and presented a dispersion-like shape when the green spot was exactly in the middle of the phase reference and sensitive probe laser beam. The dependence of the signal as a function of the modulation frequency showed the expected decrease of the signal with frequency, in full agreement with numerical simulations based on the heat diffusion.

Comparative experiments between ordinary DIC imaging of scatterers like latex spheres with 300 nm diameter compared with gold nanoparticles with 80 nm and 10 nm in diameter have shown that only absorbing objects with high saturation intensities will appear in the photothermal image under our present conditions. In biological samples in particular, the absorption background from fluorescent labeling or from absorbing biomolecules appears to be utterly negligible.

The photothermal detection of small absorbing labels, being based on different principles, it presents definite advantages over fluorescence. The method and mode of operation of the devices of the invention is background-free, even in given environments. There is neither photobleaching, nor saturation for illumination intensities up to several tens of MW/cm$^2$. To the knowledge of inventors, no other optical method, not even near-field optics appears to be able to detect non-fluorescing objects as small as 2.5 nm. This represents a gain of more than three orders of magnitude in volume over the current optical detection by plasmon Rayleigh given.

In the present experiments, the temperature rise of metal particles with 5 nm diameter has been estimated to about 15 K. Because the temperature rise falls off as the reciprocal distance from the particle's center, it decreases to 3 K 13 nm away from the center. Although small, this temperature rise might still be too high for some proteins or biomolecules. However, it is believed that S/N can be significantly improved in a transmission geometry and by reaching the photon noise in detecting the sensitive probe laser beams.

We claim:

1. A method for photothermal imaging tiny metal particles immersed in a given medium, said method comprising at least:

illuminating said given medium and immersed tiny particles through separate phase reference laser beam and sensitive probe laser beam, said sensitive probe laser beam undergoing through impingement of said sensitive probe laser beam on said given medium slight phase changes induced by photothermal effect due to a local heating within said given medium in the absence of any substantial phase changes to said phase reference laser beam;

detecting said slight phase changes on said sensitive probe laser beam with reference to said phase reference laser beam through differential phase interference contrast phenomenon, thereby allowing each of said tiny metal particles immersed in said given medium to be imaged as an optical label.

2. The method of claim 1, wherein illuminating said given medium and immersed tiny particles comprises:

splitting a probe laser beam into a first and second probe laser beam, said first and second probe laser beam undergoing the same phase relationship on separate optical paths;

superimposing on one of said first and second probe laser beam a heating laser beam propagating on the same optical path as that of said one of said first and second probe laser beam on which it is superimposed, said one of said first and second probe laser beam and superimposed heating laser beam forming said sensitive probe laser beam and the other of said one of said first and second probe laser beam forming said phase reference laser beam.

3. The method of claim 2, said method further including:

amplitude modulating said heating laser beam at a given frequency; and synchronously detecting said slight phase changes through differential phase interference contrast phenomenon.

4. The method of claim 3, in which said given frequency is executed at a frequency between 100 kHz and 10 MHz, said frequency being such that a given volume of said given medium overlaps the focal spot of said sensitive probe laser beam focused on said given medium.

5. The method of claim 1, wherein said method comprises at least: illuminating said given medium and immersed tiny particles through separate phase reference laser beam and sensitive probe laser beam, so as to generate a reflected phase reference laser beam and a reflected sensitive probe laser beam, said reflected sensitive probe laser beam undergoing through impingement of said sensitive probe laser beam on said given medium slight phase changes induced by photothermal effect due to a local heating within said given medium in the absence of any substantial phase changes to said reflected phase reference laser beam;

detecting said slight phase changes on said reflected sensitive probe laser beam with reference to said reflected phase reference laser beam through differential phase interference contrast phenomenon, thereby allowing each of said tiny metal particles immersed in said given medium to be imaged as an optical label.

6. The method of claim 5, wherein detecting said slight phase changes on said reflected sensitive probe laser beam with reference to said reflected phase reference laser beam comprises at least:

focusing back said reflected phase reference laser beam and reflected sensitive probe laser beam along corresponding optical paths of said first and second probe laser beam;

recombining said focused reflected phase reference and reflected sensitive probe laser beam to a unique sensing laser beam in which said differential phase interference phenomenon is induced.

7. The method of claim 1, in which said tiny metal particles are nanometer particles.

8. A device for photothermal imaging of tiny metal particles immersed in a given medium, said device comprising at least means for illuminating part of said given medium and immersed tiny particles through separate phase reference laser beam and sensitive probe laser beam, said sensitive probe laser beam undergoing through impingement of said sensitive probe laser beam on said given medium slight phase changes induced by photothermal effect due to a local heating within said given medium in the absence of any substantial phase changes to said phase reference laser beam;

means for detecting said slight phase changes on said sensitive probe laser beam with reference to said phase reference laser beam through a differential phase interference contrast phenomenon;

means for imaging each of said tiny metal particles immersed in said given medium as an optical label from said differential phase interference contrast phenomenon.

9. The device of claim 8, in which said means for illuminating comprises at least:

a probing laser generator adapted to generate a probe laser beam;

means for splitting said probe laser beam to a first and a second probe laser beam, said first and second probe laser beam undergoing the same phase relationship on separate optical paths;

means for generating a heating laser beam;

means for superimposing said heating laser beam on one of said first and second probe laser beam with the superimposed heating laser beam propagating on the same optical path as that of said one of said first and second probe laser beam onto which it is superimposed, said superimposed heating laser beam and one of said first and second probe laser beam propagating onto the same optical path thus constituting said sensitive probe laser beam and the other of said one of said first and second probe laser beam separate from said same optical path constituting said phase reference laser beam;

means for focusing said phase reference laser beam and said sensitive probe laser beam at separate location on said given medium.

10. The device of claim 9, in which for a given medium deposited on a glass cover slip, said device further includes at least:

a 3D moving table, in given reference directions, two of said reference directions being substantially parallel to the input face of said glass cover slip and the third one of said reference directions being substantially perpendicular to said glass cover slip;

an objective lens mounted on said 3D moving table, said objective lens and 3D moving table being thus adapted to focusing said separate laser beam and sensitive probe laser beam on said given medium deposited on said black screen, so as to generate reflected a phase reference laser beam and a reflected sensitive laser beam undergoing said slight phase changes induced by photothermal effect due to a local heating reflected by said given medium.

11. The device of claim 10, wherein said means for detecting said slight phase changes onto said reflected sensitive probe laser beam comprise at least:

means for focusing back said reflected phase reference laser beam and reflected sensitive probe laser beam along corresponding optical paths of said first and second probe laser beam;

means for recombining said focused reflected phase reference and reflected sensitive probe laser beam to a unique sensing laser beam in which said differential phase interference phenomenon is induced.

12. The device of claim 9, wherein said means for superimposing, said means for focusing and said means for focusing back are common so as to form a telecentric system.

13. The device of claim 9, wherein said means for splitting and said means for recombining are common and include a polarizing cube and a Wollaston prism.

14. A method for photothermal imaging tiny metal particles immersed in a given medium, said method comprising at least:

illuminating said given medium and immersed tiny particles through separate phase reference laser beam and sensitive probe laser beam, said sensitive probe laser beam undergoing through impingement of said sensitive probe laser beam on said given medium slight phase changes induced by photothermal effect due to a local heating within said given medium in the absence of any substantial phase changes to said phase reference laser beam;

detecting said slight phase changes on said sensitive probe laser beam with reference to said phase reference laserbeam through differential phase interference contrast phenomenon, thereby allowing each of said tiny metal particles immersed in said given medium.

15. The device of claim 11, wherein said means for superimposing, said means for focusing and said means for focusing back are common so as to form a telecentric system.

16. The device of claim 11, wherein said means for splitting and said means for recombining are common and include a polarizing cube and a Wollaston prism.

* * * * *